(12) United States Patent
Heckroth et al.

(10) Patent No.: US 9,421,298 B2
(45) Date of Patent: *Aug. 23, 2016

(54) TISSUE ADHESIVE BASED ON NITROGEN-MODIFIED ASPARTATES

(75) Inventors: Heike Heckroth, Odenthal (DE); Christoph Eggert, Köln (DE)

(73) Assignee: Adhesys Medical GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/984,186

(22) PCT Filed: Feb. 6, 2012

(86) PCT No.: PCT/EP2012/051914
§ 371 (c)(1),
(2), (4) Date: Aug. 7, 2013

(87) PCT Pub. No.: WO2012/107375
PCT Pub. Date: Aug. 16, 2012

(65) Prior Publication Data
US 2013/0325062 A1    Dec. 5, 2013

(30) Foreign Application Priority Data
Feb. 9, 2011 (EP) .................................. 11153810

(51) Int. Cl.
| | | |
|---|---|---|
| C08L 75/02 | (2006.01) | |
| C08L 75/04 | (2006.01) | |
| C09D 175/02 | (2006.01) | |
| C08G 18/10 | (2006.01) | |
| A61L 24/04 | (2006.01) | |
| C08G 18/38 | (2006.01) | |
| C08G 18/42 | (2006.01) | |
| C08G 18/73 | (2006.01) | |
| A61L 24/00 | (2006.01) | |

(52) U.S. Cl.
CPC ........... *A61L 24/046* (2013.01); *A61L 24/0015* (2013.01); *C08G 18/10* (2013.01); *C08G 18/3821* (2013.01); *C08G 18/4252* (2013.01); *C08G 18/73* (2013.01)

(58) Field of Classification Search
None
See application file for complete search history.

(56) References Cited

U.S. PATENT DOCUMENTS

| | | | | |
|---|---|---|---|---|
| 3,479,310 A * | 11/1969 | Bayer et al. | ..................... | 524/591 |
| 3,886,122 A * | 5/1975 | Fabris et al. | ..................... | 528/53 |
| 4,040,992 A * | 8/1977 | Bechara et al. | ................ | 521/117 |
| 4,190,566 A * | 2/1980 | Noll et al. | ..................... | 524/839 |
| 4,334,944 A * | 6/1982 | Creyf | ......................... | 156/308.2 |
| 4,501,852 A * | 2/1985 | Markusch et al. | ............ | 524/591 |
| 4,587,149 A * | 5/1986 | Murachi | ......................... | 428/90 |
| 5,126,170 A * | 6/1992 | Zwiener et al. | ............. | 427/385.5 |
| 5,236,741 A * | 8/1993 | Zwiener et al. | ............. | 427/385.5 |
| 5,243,012 A * | 9/1993 | Wicks et al. | .................... | 528/58 |
| 5,397,930 A * | 3/1995 | Nilssen | ......................... | 307/150 |
| 5,594,097 A * | 1/1997 | Chaffanjon et al. | .......... | 528/419 |
| 5,736,604 A * | 4/1998 | Luthra | .......................... | 524/591 |
| 5,925,781 A * | 7/1999 | Pantone et al. | ................. | 560/26 |
| 6,296,607 B1 * | 10/2001 | Milbocker | ...................... | 600/30 |
| 6,359,101 B1 * | 3/2002 | O'Connor et al. | ............. | 528/66 |
| 6,458,293 B1 * | 10/2002 | Roesler et al. | ........... | 252/182.23 |
| 6,482,333 B1 * | 11/2002 | Roesler et al. | ........... | 252/182.12 |
| 7,754,782 B2 * | 7/2010 | Heckroth et al. | ............. | 523/111 |
| 8,168,431 B2 * | 5/2012 | Brady et al. | ................... | 435/396 |
| 2003/0135238 A1 * | 7/2003 | Milbocker | ...................... | 606/231 |
| 2004/0067315 A1 * | 4/2004 | Niesten et al. | .............. | 427/372.2 |
| 2004/0157945 A1 * | 8/2004 | Barber | .......................... | 521/155 |
| 2005/0129733 A1 * | 6/2005 | Milbocker et al. | ............. | 424/423 |
| 2006/0058410 A1 * | 3/2006 | Yu et al. | ........................ | 521/155 |
| 2007/0003594 A1 * | 1/2007 | Brady et al. | ................... | 424/426 |
| 2007/0160851 A1 * | 7/2007 | Barancyk et al. | .......... | 428/423.1 |
| 2008/0067720 A1 * | 3/2008 | Wiese et al. | .................... | 264/334 |
| 2008/0145696 A1 * | 6/2008 | Senkfor et al. | ................. | 428/687 |
| 2009/0012206 A1 * | 1/2009 | Heckroth et al. | ............. | 523/111 |
| 2009/0191145 A1 | 7/2009 | Heckroth et al. | | |
| 2009/0221071 A1 * | 9/2009 | Heckroth et al. | ............. | 435/375 |
| 2011/0123479 A1 | 5/2011 | Heckroth et al. | | |
| 2012/0178847 A1 | 7/2012 | Heckroth et al. | | |

FOREIGN PATENT DOCUMENTS

| | | |
|---|---|---|
| EP | 2083025 A1 | 7/2009 |
| EP | 2097466 A2 | 9/2009 |
| EP | 2145634 A1 | 1/2010 |
| EP | 2275466 A1 | 1/2011 |
| WO | WO-2008076707 A2 | 6/2008 |
| WO | WO-2009106245 A2 | 9/2009 |

OTHER PUBLICATIONS

PEG 300 Aldrich, Aug. 10, 2014.*
Poly(ethylene glycol) 300 Sigma Aldrich TDS, Aug. 10, 2014.*

* cited by examiner

*Primary Examiner* — Peter A Salamon
(74) *Attorney, Agent, or Firm* — Drinker Biddle & Reath LLP

(57) ABSTRACT

The invention relates to a polyurea system comprising as component A) isocyanate-functional prepolymers which can be obtained by reacting aliphatic isocyanates A1) with polyols A2) that can have a number-average molecular weight of =400 g/mol and an average OH functionality of 2 to 6 in particular; and as component B) amino-functional aspartic acid esters of the general formula (I) in which X is an organic group containing a secondary amino function, R1, R2 are the same or different organic groups that do not have Zerewitinoff-active hydrogen, and n is a whole number of at least 2, in particular for sealing, bonding, gluing, or covering cell tissue. The invention also relates to a metering system for the polyurea system according to the invention.

21 Claims, No Drawings

TISSUE ADHESIVE BASED ON NITROGEN-MODIFIED ASPARTATES

CROSS-REFERENCE TO RELATED APPLICATIONS

This application is a national stage application (under 35 U.S.C. §371) of PCT/EP2012/051914, filed Feb. 6, 2012, which claims benefit of European application 11153810.4, filed Feb. 9, 2011 which are both incorporated by reference.

The present invention relates to a polyurea system in particular for the sealing, bonding, gluing or covering of cell tissue, and to a dosing system for the polyurea system according to the invention.

Various materials which are used as tissue adhesives are commercially available. These include the cyanoacrylates Dermabond® (octyl 2-cyanoacrylate) and Histoacryl Blue® (butyl cyanoacrylate). However, a prerequisite for efficient adhesion of cyanoacrylates is dry substrates. In cases of severe bleeding, adhesives of this type fail.

Alternatives to the cyanoacrylates that are available are biological adhesives such as, for example, BioGlue®, a mixture of glutaraldehyde and bovine serum albumin, various collagen- and gelatin-based systems (FloSeal®) and also the fibrin adhesives (Tissucol). These systems serve primarily to stop bleeding (hemostasis). Besides the high costs, fibrin adhesives are characterized by a relatively weak adhesive strength and a rapid degradation, meaning that they can only be used for relatively small injuries on unstretched tissue. Collagen- and gelatin-based systems such as FloSeal® serve exclusively for hemostasis. Moreover, since fibrin and thrombin are obtained from human material, and collagen and gelatin are obtained from animal material, there is always the risk with biological systems of an infection. Furthermore, biological systems have to be stored under cool conditions, meaning that use in emergency care such as e.g. in catastrophe regions, for military deployment etc. is not possible. Here, QuikClot® or QuikClot ACS+™ is available for treating trauma wounds and is mineral granules which, in an emergency, is introduced into the wound where it leads to coagulation as a result of water extraction. In the case of QuikClot®, this is an extremely exothermic reaction, which leads to burns. QuikClot ACS+™ is a gauze in which the salt is embedded. The system has to be firmly pressed onto the wound to stop bleeding.

WO 2009/106245 A2 discloses the production and use of polyurea systems as tissue adhesives. The systems disclosed herein comprise at least two components. These are an amino-functional aspartic acid ester and an isocyanate-functional prepolymer which is obtainable by reacting aliphatic polyisocyanates with polyesterpolyols. The described 2-component polyurea systems can be used as tissue adhesives for sealing wounds in human and animal cell aggregations. A very good adhesive result can be achieved here.

In order to ensure good miscibility of the two components of the polyurea system, the viscosity of the components at 23° C. should as far as possible be less than 10 000 mPas. Prepolymers with NCO functionalities of less than 3 have a correspondingly low viscosity. If prepolymers of this type are used, it is necessary to use, as second component, an aspartic acid ester with an amino functionality of more than 2 since otherwise no polymeric network can be produced. However, this is a requirement so that the polyurea system or an adhesive suture consisting thereof has the desired mechanical properties such as elasticity and durability. Moreover, it is disadvantageous when using difunctional aspartic acid esters that the curing time is up to 24 h, with the polyurea system in many cases remaining tacky even after this time, i.e. is not tack-free.

It was therefore an object of the invention to provide a polyurea system which has good miscibility and fully reacts rapidly with the formation of a three-dimensional polyurea network. An additional condition to be ensured here is that the cured system has no cytotoxicity in accordance with ISO 10993 when used on people or animals.

According to the invention, this object is achieved by a polyurea system comprising
as component A) isocyanate-functional prepolymers obtainable by reacting
aliphatic isocyanates A1) with
polyols A2), which in particular can have a number-average molecular weight of ≥400 g/mol and an average OH functionality of 2 to 6,
as component B) amino-functional aspartic acid esters of the general formula (I)

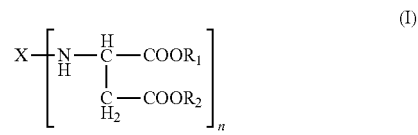

in which
X is an organic radical containing a secondary amino function,
$R_1$, $R_2$ are identical or different organic radicals which have no zerewitinoff-active hydrogen and
n is an integer of at least 2.

The components of the polyurea system according to the invention can readily be mixed together since they have a viscosity of less than 10 000 mPas at 23° C. Moreover, they are able to rapidly form a three-dimensional polyurea network after mixing. This network is characterized by high elasticity, durability, adhesive strength and a lack of cytotoxicity. Moreover, even after a short time, the network is no longer tacky, i.e. is tack-free.

Particularly preferably, n in the formula (I) is an integer ≥2≤4 and very particularly preferably 2.

According to a further preferred embodiment of the polyurea system according to the invention, X is a radical of the formula (II)

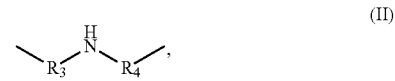

in which
$R_3$, $R_4$ in each case independently of one another are an organic radical which has no zerewitinoff-active hydrogen.

It is particularly preferred here if R3, R4, in each case independently of one another or simultaneously, are a linear or branched, saturated organic radical optionally also substituted in the chain with heteroatoms, in particular a linear or branched, saturated, aliphatic C1 to C10, preferably C2 to C8 and very particularly preferably C2 to C6 hydrocarbon radical. Polyurea systems of this type cure particularly rapidly.

A likewise advantageous polyurea system is one comprising a compound of the formula (I) in which the radicals $R_1$, $R_2$, in each case independently of one another, are linear or branched C1 to C10, preferably C1 to C8, particularly preferably C2 to C6, very particularly preferably C2 to C4, organic radicals and in particular aliphatic hydrocarbon radicals. Examples of particularly suitable radicals are methyl, ethyl, propyl and butyl.

The polyurea systems according to the invention are obtained by mixing the prepolymers A) with the aminofunctional compound B) and optionally the components C), D) and/or E). The ratio of free or blocked amino groups to free NCO groups here is preferably 1:1.5, particularly preferably 1:1. Water and/or amine are admixed here to component B) and/or C b).

The isocyanate-functional prepolymers A) are obtainable by reacting polyisocyanates A1) with polyols A2) optionally with the addition of catalysts and also auxiliaries and additives.

Polyisocyanates A1) which can be used are, for example, monomeric aliphatic or cycloaliphatic di- or triisocyanates such as 1,4-butylene diisocyanate (BDI), 1,6-hexamethylene diisocyanate (HDI), isophorone diisocyanate (IPDI), 2,2,4- and/or 2,4,4-trimethylhexamethylene diisocyanate, the isomeric bis(4,4'-isocyanatocyclohexyl)methanes or mixtures thereof with any desired isomer content, 1,4-cyclohexylene diisocyanate, 4-isocyanatomethyl 1,8-octane diisocyanate (nonane triisocyanate), and also alkyl 2,6-diisocyanatohexanoate (lysine diisocyanate) with C1-C8-alkyl groups.

Besides the aforementioned monomeric polyisocyanates A1), it is also possible to use their high molecular weight consecutive products with uretdione, isocyanurate, urethane, allophanate, biuret, iminooxadiazinedione or oxadiazinetrione structure, and mixtures thereof.

Preference is given to using polyisocyanates A1) of the aforementioned type with exclusively aliphatically or cycloaliphatically bonded isocyanate groups or mixtures thereof.

It is likewise preferred if polyisocyanates A1) of the above type with an average NCO functionality of from 1.5 to 2.5, preferably from 1.6 to 2.4, further preferably from 1.7 to 2.3, very particularly preferably from 1.8 to 2.2 and especially of 2 are used.

Very particular preference is given to using hexamethylene diisocyanate as polyisocyanate A1).

According to one preferred embodiment of the polyurea system according to the invention, it is provided that the polyols A2) are polyesterpolyols and/or polyester-polyetherpolyols and/or polyetherpolyols. Particular preference is given here to polyester-polyether-polyols and/or polyetherpolyols with an ethylene oxide fraction between 60 and 90% by weight.

It is also preferred if the polyols A2) have a number-average molecular weight of 4000 to 8500 g/mol.

Suitable polyether ester polyols are prepared according to the prior art preferably by polycondensation from polycarboxylic acids, anhydrides of polycarboxylic acids, and also esters of polycarboxylic acids with readily volatile alcohols, preferably C1 to C6 monools, such as methanol, ethanol, propanol or butanol, with molar excess, low molecular weight and/or higher molecular weight polyol; where polyols containing ether groups, optionally in mixtures with other polyols free from ether groups, are used as polyols.

It is of course also possible to use mixtures of higher molecular weight and lower molecular weight polyols for the polyether ester synthesis.

Such molar excess low molecular weight polyols are polyols with molar masses from 62 to 299 daltons, having 2 to 12 carbon atoms and hydroxyl functionalities of at least 2, which may also be branched or unbranched and whose hydroxyl groups are primary or secondary. These low molecular weight polyols can also have ether groups. Typical representatives are ethylene glycol, propanediol-1,2, propanediol-1,3, butanediol-1,4, butanediol-2,3,2-methylpropanediol-1,3, pentanediol-1,5, hexanediol-1,6,3-methylpentanediol-1,5,1, 8-octanediol, 1,10-decanediol, 1,12-dodecanediol, cyclohexanediol, diethylene glycol, triethylene glycol and higher homologs, dipropylene glycol, tripropylene glycol and higher homologues, glycerol, 1,1,1-trimethylolpropane, and also oligotetrahydrofurans with hydroxyl end groups. Mixtures within this group can of course also be used.

Molar excess higher molecular weight polyols are polyols with molar masses of from 300 to 3000 daltons which can be obtained by ring-opening polymerization of epoxides, preferably ethylene oxide and/or propylene oxide, and also by acid-catalyzed, ring-opening polymerization of tetrahydrofuran. For the ring-opening polymerization of epoxides it is possible to use either alkali metal hydroxides or double metal cyanide catalysts.

Starters for ring-opening epoxide polymerizations which can be used are all at least bifunctional molecules from the group of amines and the aforementioned low molecular weight polyols. Typical representatives are 1,1,1-trimethylolpropane, glycerol, o-TDA, ethylenediamine, propyleneglycol-1,2, etc., and water, including mixtures thereof. Within the group of excess higher molecular weight polyols, it is of course also possible to use mixtures.

The structure of the higher molecular weight polyols, insofar as they are polyalkylene oxides of ethylene oxide and/or propylene oxide terminated with hydroxyl groups, may take place statistically or blockwise, in which case mixed blocks may also be present.

Polycarboxylic acids are both aliphatic and aromatic carboxylic acids which may either be cyclic, linear, branched or unbranched and which can have between 4 and 24 carbon atoms.

Examples are succinic acid, glutaric acid, adipic acid, azelaic acid, sebacic acid, 1,10-decanedicarboxylic acid, 1,12-dodecanedicarboxylic acid, phthalic acid, terephthalic acid, isophthalic acid, trimellitic acid, pyromellitic acid. Preference is given to succinic acid, glutaric acid, adipic acid, sebacic acid, lactic acid, phthalic acid, terephthalic acid, isophthalic acid, trimellitic acid, pyromellitic acid. Particular preference is given to succinic acid, glutaric acid and adipic acid.

Furthermore, the group of polycarboxylic acids also comprises hydroxycarboxylic acids, or their internal anhydrides, such as e.g. caprolactone, lactic acid, hydroxybutyric acid, ricinoleic acid, etc. Furthermore included are monocarboxylic acids, in particular those which have more than 10 carbon atoms, such as soybean oil fatty acid, palm oil fatty acid and peanut oil fatty acid, where their fraction relative to the whole reaction mixture forming the polyether ester polyol does not exceed 10% by weight and additionally the low functionality associated therewith is balanced by co-using at least trifunctional polyols whether on sides of the low molecular weight or of the high molecular weight polyols.

According to the prior art, the preparation of the polyether ester polyols takes place at elevated temperature in the range from 120 to 250° C., firstly under atmospheric pressure, later by applying a vacuum from 1 to 100 mbar, preferably, but not necessarily using an esterification or transesterification catalyst, the reaction being completed such that the acid number drops to values of from 0.05 to 10 mg KOH/g, preferably 0.1 to 3 mg KOH/g and particularly preferably 0.15 to 2.5 mg KOH/g.

Furthermore, in the course of the atmospheric-pressure phase before applying a vacuum, an inert gas can be used. Alternatively or for individual phases of the esterification, it is of course also possible to use liquid or gaseous entrainers. For example, the water of reaction can likewise be discharged using nitrogen as carrier gas, as well as using an azeotrope entrainer, such as e.g. benzene, toluene, xylene, dioxane, etc.

Mixtures of polyetherpolyols with polyesterpolyols can of course also be used in any desired ratios.

Polyetherpolyols are preferably polyalkylene oxide polyethers based on ethylene oxide and optionally propylene oxide.

These polyetherpolyols are preferably based on di- or higher-functional starter molecules such as di- or higher-functional alcohols or amines.

Examples of such starters are water (regarded as diol), ethylene glycol, propylene glycol, butylene glycol, glycerol, TMP, sorbitol, pentaerythritol, triethanolamine, ammonia or ethylenediamine.

Polycarbonates having hydroxyl groups, preferably polycarbonatediols, with number-average molecular weights $M_n$ of from 400 to 8000 g/mol, preferably 600 to 3000 g/mol, can likewise be used. These are obtainable by reacting carbonic acid derivatives, such as diphenyl carbonate, dimethyl carbonate or phosgene, with polyols, preferably diols.

Examples of such diols are ethylene glycol, 1,2- and 1,3-propanediol, 1,3- and 1,4-butanediol, 1,6-hexanediol, 1,8-octanediol, neopentyl glycol, 1,4-bishydroxymethylcyclohexane, 2-methyl-1,3-propanediol, 2,2,4-trimethylpentanediol-1,3, dipropyleneglycol, polypropylene glycols, dibutyleneglycol, polybutyleneglycols, bisphenol A and lactone-modified diols of the aforementioned type.

To produce the prepolymer A), the polyisocyanate A1) can be reacted with the polyol A2) at a NCO/OH ratio of preferably 4:1 to 12:1, particularly preferably 8:1, and then the fraction of unreacted polyisocyanate can be separated off by means of suitable methods. Usually, thin-film distillation is used for this purpose, giving prepolymers with residual monomer contents of less than 1% by weight, preferably less than 0.1% by weight, very particularly preferably less than 0.03% by weight.

Optionally, stabilizers such as benzoyl chloride, isophthaloyl chloride, dibutyl phosphate, 3-chloropropionic acid or methyl tosylate can be added during the preparation.

The reaction temperature during the preparation of the prepolymers A) here is preferably 20 to 120° C. and further preferably 60 to 100° C.

The prepared prepolymers have an average NCO content, measured in accordance with DIN EN ISO 11909, of from 2 to 10% by weight, preferably 2.5 to 8% by weight.

According to a further embodiment of the polyurea system according to the invention, the prepolymers A) can have an average NCO functionality of from 1.5 to 2.5, preferably from 1.6 to 2.4, further preferably from 1.7 to 2.3, very particularly preferably from 1.8 to 2.2 and especially of 2.

The organic fillers of component C) may be preferably hydroxy-functional compounds, in particular polyetherpolyols with repeating ethylene oxide units.

It is also advantageous if the fillers of component C) have an average OH functionality of from 1.5 to 3, preferably of from 1.8 to 2.2 and particularly preferably of 2.

For example, organic fillers which can be used are polyethyleneglycols that are liquid at 23° C., such as PEG 200 to PEG 600, the mono- or dialkylethers thereof such as PEG 500 dimethylether, liquid polyether- and polyesterpolyols, liquid polyester such as e.g. Ultramoll (Lanxess AG, Leverkusen, Germany), and glycerol and its liquid derivatives such as e.g. triacetin (Lanxess AG, Leverkusen, Germany).

The viscosity of the organic fillers, measured in accordance with DIN 53019 at 23° C., is preferably 50 to 4000 mPas, particularly preferably 50 to 2000 mPas.

In a preferred embodiment of the polyurea system according to the invention, the organic fillers used are polyethyleneglycols. These preferably have a number-average molecular weight of from 100 to 1000 g/mol, particularly preferably 200 to 400 g/mol.

In order to further reduce the average equivalent weight of the compounds used overall for the prepolymer crosslinking, based on the NCO-reactive groups, it is possible to additionally prepare reaction products of the prepolymers A) with the amino-functional compound B) and/or the organic fillers C), if these are amino- or hydroxy-functional, in a separate pre-reaction and then to use these as higher molecular weight curing component.

Preferably, during the preextension, ratios of isocyanate-reactive groups to isocyanate groups of from 50:1 to 1.5:1, particularly preferably 15:1 to 4:1, are established.

An advantage of this modification through preextension is that the equivalent weight and the equivalent volume of the hardener component can be modified within greater limits. Consequently it can be used for the application of commercially available 2-chamber dosing systems in order to obtain an adhesive system which, in the case of existing ratios of the chamber volumes, can be adjusted to the desired ratio of NCO-reactive groups to NCO groups.

According to a further preferred embodiment of the polyurea system according to the invention, it is provided that the component E) comprises a tertiary amine of the general formula (III)

in which
$R_5$, $R_6$, $R_7$ independently of one another can be alkyl or heteroalkyl radicals having heteroatoms in the alkyl chain or at their end, or $R_7$ and $R_8$, together with the nitrogen atom carrying them, can form an aliphatic, unsaturated or aromatic heterocycle which can optionally contain further heteroatoms.

These polyurea systems are characterized by particularly rapid curing.

The compounds used in component E) may be very particularly preferably tertiary amine selected from the group triethanolamine, tetrakis(2-hydroxyethyl)ethylenediamine, N,N-dimethyl-2-(4-methylpiperazin-1-yl)ethanamine, 2-{[2-(dimethylamino)ethyl](methyl)amino}ethanol, 3,3',3"-(1,3,5-triazinane-1,3,5-triyl)tris(N,N-dimethylpropan-1-amine).

Very particularly high curing rates can also be achieved if the component E) comprises 0.2 to 2.0% by weight of water and/or 0.1 to 1.0% by weight of the tertiary amine.

The polyurea systems can of course also comprise pharmacologically active ingredients such as analgesics with or without antiinflammatory effect, antiphlogistics, antimicrobially effective substances, antimycotics, antiparasitic substances.

The polyurea system according to the invention is particularly suited for the sealing, bonding, gluing or covering of cell tissue and in particular for stemming the escape of blood or tissue fluids and the sealing of leakages in cell tissue. It can be used very particularly preferably for the use or preparation of a means for the sealing, binding, gluing or covering of human or animal cell tissue. It can be used to produce rapidly curing, transparent, flexible and biocompatible adhesive sutures that exhibit strong adhesion to the tissue.

The invention yet further provides a dosing system with two chambers for a polyurea system according to the invention in which, in the one chamber, the component A) is present and, in the other chamber, the components B) and optionally the components C), D) and E) of the polyurea system are present. A dosing system of this type is suitable in particular for applying the polyurea system as adhesive to tissue.

EXAMPLES

Methods

Molecular weight: The molecular weights were determined by means of gel permeation chromatography (GPC) as follows: Calibration is with polystyrene standard with molecular weights of Mp 1 000 000 to 162. The eluent used was tetrahydrofuran p.A. The following parameters were maintained during the double measurement: Degassing: Online degasser; flow rate: 1 ml/min; analysis time: 45 minutes; detectors: refractometer and UV detector; injection volume: 100 µl-200 µl. The molar mass averages Mw; Mn and Mp and also the polydispersity Mw/Mn were calculated with the assistance of software. Baseline points and evaluation limits were established in accordance with DIN 55672 part 1.

NCO content: unless expressly mentioned otherwise, determined volumetrically in accordance with DIN-EN ISO 11909.

Viscosity: was determined in accordance with ISO 3219 at 23° C.

Residual monomer content: was carried out in accordance with DIN ISO 17025

NMR: was determined using a Bruker DRX 700 instrument.

Substances:

HDI: Hexamethylene diisocyanate (Bayer MaterialScience AG)

Polyethylene glycol 600 (Aldrich)

Polyethylene glycol 400 (Aldrich)

Polyethylene glycol 200 (Aldrich)

Synthesis of triethyl 4-oxo-3-oxa-7,11,16-triazaoctadecane-6,17,18-tricarboxylate (spermidine aspartate) (1)

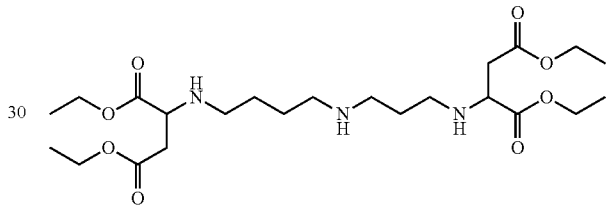

11.9 g (69 mmol) of diethyl maleate were added to a solution of 5 g (34.5 mmol) of spermidine in 5 ml of THF. The reaction mixture was stirred for 3 days at 60° C. After removing the solvent in vacuo, the product was obtained quantitatively as a yellow liquid.

$^1$H-NMR (CDCl$_3$, 700 MHz): δ=1.27 (t, 6H), 1.29 (t, 6H), 1.49 (br, 3NH), 1.62 (m, 6H) 2.62 (m, 12H), 3.60 (t, 2H), 4.13 (q, 4H), 4.2 (q, 4H).

$^{13}$C-NMR (CDCl$_3$, 700 MHz): 13.7, 27.3, 27.4, 29.8, 37.6, 46.1, 47.4, 47.7, 49.3, 57.3, 59.9, 60.1, 170.9, 173.1.

Synthesis of triethyl 4-oxo-3-oxa-7,14,21-triazatricosane-6,22,23-tricarboxylate (2)

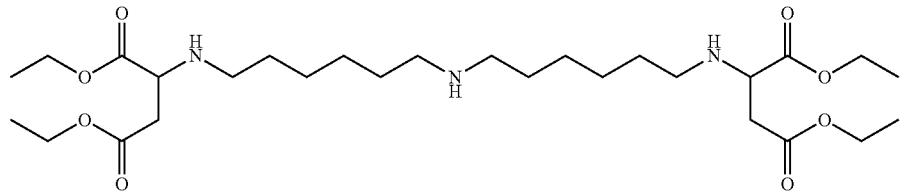 [SMILES: CCOC(=O)CC(NCCCCCCNCCCCCCNC(CC(=O)OCC)C(=O)OCC)C(=O)OCC]

Analogously to (1), 154 g (0.72 mol) of bis(hexamethylene)triamine and 246 g (1.42 mol) of diethyl maleate were used to obtain 400 g of the product as a yellow liquid.

$^1$H-NMR (CDCl$_3$, 700 MHz): δ=1.27 (t, 6H), 1.29 (t, 6H), 1.34 (m, 8H), 1.49 (br, 3NH), 2.59 (m, 12H), 3.70 (t, 2H), 4.11 (q, 4H), 4.2 (q, 4H).

$^{13}$C-NMR (CDCl$_3$, 700 MHz): 14.1, 26.8, 27.1, 30.0, 30.1, 38.1, 47.9, 50.1, 57.8, 60.3, 60.8, 170.7, 172.7.

Triethyl 4-oxo-3-oxa-7,11,15-triazaheptadecane-6,16,17-tricarboxylate (3)

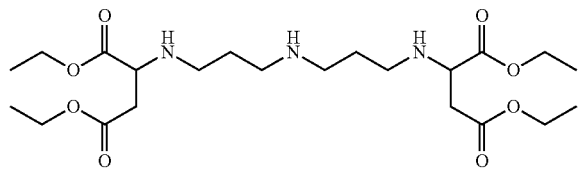 [SMILES: CCOC(=O)CC(NCCCNCCCNC(CC(=O)OCC)C(=O)OCC)C(=O)OCC]

Analogously to (1), 3.9 g (0.03 mol) of bis(3-aminopropyl)amine and 10.33 g (0.06 mol) of diethyl maleate were used to obtain 14.23 g of the product as a yellow liquid.

$^1$H-NMR (CDCl$_3$, 700 MHz): δ=1.26 (t, 6H), 1.27 (t, 6H), 1.49 (br, 3NH), 1.62 (m, 4H), 2.61 (m, 12H), 3.60 (t, 2H), 4.15 (q, 4H), 4.19 (q, 4H).

$^{13}$C-NMR (CDCl$_3$, 700 MHz): 14.2, 14.4, 27.9, 30.3, 38.1, 46.5, 48.1, 49.9, 57.8, 60.4, 61.0, 170.8, 173.2.

Synthesis of Prepolymer A 212.5 g (1.8 mol) of succinic acid were heated with stirring to 235° C. with 1591.5 g of polyethyleneglycol 600 (2.6 mol). Here, the water which formed was distilled off over 8.5 h. 100 ppm of tin(II) chloride were then added and the mixture was heated at 235° C. for a further 9 h in vacuo (15 mbar) on a water separator.

672 g of HDI (4 mol) were charged with 0.1% by weight of benzoyl chloride and heated to 80° C. Then, with stirring, 788 g of the polyester prepared above were metered in over 1 h and the mixture was further stirred at 80° C. until a constant NCO content was reached. The excess HDI was removed at 140° C. and 0.13 mbar by means of a thin-film evaporator. The resulting prepolymer had an NCO content of 3.5% and a viscosity of 4700 mPas/23° C. The residual monomer content was <0.03% HDI.

Synthesis of Prepolymer B

Analogously to prepolymer A, the corresponding polyester was prepared from 263 g (1.8 mol) of adipic acid and 1591.5 g of polyethylene glycol 600 (2.6 mol) and reacted with HDI to give the prepolymer. The resulting prepolymer had an NCO content of 5.93% and a viscosity of 1450 mPas/23° C. The residual monomer content was <0.03% HDI.

Comparative Example of Trifunctional Esters: Synthesis of Prepolymer C

Analogously to prepolymer A, 236.2 g (2 mol) of succinic acid, 800 g of polyethylene glycol 400 (2 mol) and 29.84 g of glycerol (0.324 mol) were converted to the corresponding ester. The HDI prepolymer obtained therefrom had an NCO content of 3.2% and a viscosity of 50 100 mPas/23° C. The residual monomer content was <0.03% HDI.

Comparative Example of Trifunctional Esters: Synthesis of Prepolymer D

Analogously to prepolymer A, 141.7 g (1.2 mol) of succinic acid, 720 g of polyethylene glycol 200 (1.2 mol) and 25.42 g of glycerol (0.276 mol) were converted to the corresponding ester. The HDI prepolymer obtained therefrom had an NCO content of 2.7% and a viscosity of 42 500 mPas/23° C. The residual monomer content was <0.03% HDI.

Production of the Tissue Adhesive 4 g of the respective prepolymer were stirred thoroughly with an equivalent amount of the prepared amino-functional compound 3 in a beaker. The polyurea system was then applied directly to the muscle tissue to be glued as a thin layer. The processing time determined here was the time within which the polyurea system still had a sufficiently low viscosity that it could be applied to the tissue without problems.

The time after which the polyurea system was no longer tacky (tack-free time) was measured by means of adhesion experiments using a glass rod. For this, the glass rod was brought into contact with the layer made of the polyurea system. If it no longer stayed stuck, the system was considered to be tack-free. Additionally, the adhesive force was determined by coating two pieces of muscle tissue (1=4 cm, h=0.3 cm, w=1 cm) at the ends 1 cm wide using the polyurea system and sticking them together so that they overlap. The adhesive force of the polyurea system was tested in each case by pulling.

| | Curing agent | Processing time | Tack-free time | Adhesive force |
|---|---|---|---|---|
| Prepolymer A | 1 | 1 min 40 s | 3 min | ++ |
| Prepolymer A | 2 | 1 min | 2 min | ++ |
| Prepolymer A | 3 | 1 min 50s | 3 min | ++ |
| Prepolymer B | 1 | 1 min | 2 min 30 s | + |
| Prepolymer B | 2 | 1 min | 2 min | + |
| Prepolymer B | 3 | 1 min | 2 min 30 s | + |
| Prepolymer B (comparative example 1) | 6 | 8 min | >30 min | + |

++: very good;
+: good

Comparative Example

Difunctional Prepolymer+Difunctional Curing Agent

Instead of the described curing agent 2, the tetraethyl 2,2'-[(2-methylpentane-1,5-diyl)diimino]dibutanedioate (6) described in EP 2 145 634 was used. The processing time with prepolymer B was 8 min. The adhesive was not tack-free even after 30 min.

Measuring the Cytotoxicity of an Adhesive Prepared with (2)

The prepolymer A was cured with an equivalent amount of 2. The cytotoxicity was measured in accordance with ISO 10993-5:2009 with L929 cells. No reduction in cell viability took place. The system can therefore not be classed as being cytotoxic.

The invention claimed is:

1. A method for sealing, bonding, gluing or covering of a cell tissue comprising preparing a polyurea system comprising
   as component A) isocyanate-functional prepolymers obtained by reacting aliphatic isocyanates A1) with polyols A2),
   as component B) amino-functional aspartic acid esters of the general formula (I)

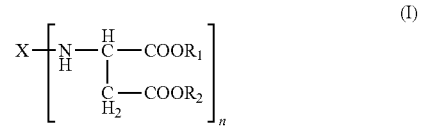

in which
   X is an organic radical containing a secondary amino function, $R_1$ and $R_2$ are identical or different organic radicals which have no zerewitinoff-active hydrogen and n is an integer of at least 2, applying the polyurea system to the cell tissue and sealing, bonding, gluing or covering the cell tissue thereby stopping the escape of blood or tissue fluids or sealing leakages in the cell tissue, wherein the polyurea system when cured has no cytotoxicity in accordance with ISO 10993.

2. The method as claimed in claim 1, wherein X is a radical of the formula (II)

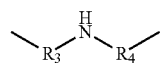

(II)

in which $R_3$ and $R_4$ in each case independently of one another, are an organic radical which has no zerewitinoff-active hydrogen.

3. The method as claimed in claim 2, wherein $R_3$ and $R_4$ in each case independently of one another or simultaneously are a linear or branched saturated organic radical optionally also substituted in the chain with heteroatoms.

4. The method as claimed in claim 1, wherein the radicals $R_1$ and $R_2$ in each case independently of one another are linear or branched C1 to C10 organic radicals.

5. The method as claimed in claim 2, wherein $R_3$ and $R_4$ in each case independently of one another or simultaneously are a linear or branched, saturated, aliphatic C2 to C6, and the radicals $R_1$ and $R_2$ in each case independently of one another are linear or branched C2 to C4 aliphatic hydrocarbon radicals.

6. The method as claimed in claim 1, wherein the polyols A2) contain polyesterpolyols and/or polyester-polyetherpolyols and/or polyetherpolyols with an ethylene oxide fraction between 60 and 90% by weight.

7. The method as claimed in claim 1, wherein the polyols A2) contain polyester-polyether-polyols and/or polyetherpolyols with an ethylene oxide fraction between 60 and 90% by weight.

8. The method as claimed in claim 1, wherein the polyols A2) have a number-average molecular weight of from 4000 to 8500 g/mol.

9. The method as claimed in claim 1, wherein it comprises, as component C), organic fillers which have a viscosity at 23° C., measured in accordance with DIN 53019, in the range from 10 to 20 000 meas.

10. The method as claimed in claim 9, wherein the organic fillers are hydroxy-functional compounds.

11. The method as claimed in claim 10, wherein the hydroxy-functional compounds are polyetherpolyols.

12. The method as claimed in claim 10, wherein the hydroxy-functional compounds have an average OH functionality of 1.5 to 3.

13. The method as claimed in claim 10, wherein the hydroxy-functional compounds have an average OH functionality of 2.

14. The method as claimed in claim 1, wherein it comprises, as component D) water and/or a tertiary amine, where the tertiary amine is selected from the group consisting of triethanolamine, tetrakis(2-hydroxyethyl)ethylenediamine, N,N-dimethyl-2-(4-methylpiperazin-1-yl)ethanamine, 2-{[2-(dimethylamino)ethyl](methyl)amino}ethanol and 3,3',3"-(1,3,5-triazinane-1,3,5-triyl)tris(N,N-dimethylpropan-1-amine).

15. The method as claimed in claim 14, wherein the system comprises 0.2 to 2.0% by weight of water and/or 0.1 to 1.0% by weight of the tertiary amine.

16. The method as claimed in claim 1, wherein it comprises, as component E) pharmacologically active compounds.

17. The method as claimed in claim 1, wherein it comprises, as component E) analgesics with or without antiinflammatory effect, antiphlogistics, antimicrobially effective substances or antimycotics.

18. The method as claimed in claim 1, wherein said polyols A2) have a number-average molecular weight of ≥400 g/mol and an average OH functionality of 2 to 6.

19. The method according to claim 1, wherein the polyurea system is applied with a dosing system, wherein the dosing system comprises two chambers for the polyurea system wherein, in the one chamber, the component A) is present and, in the other chamber, the components B) and optionally the components C), D) and E) of the polyurea system are present.

20. The method as claimed in claim 1, wherein component A1) is hexamethylene diisocyanate and component B) is selected from the group consisting of triethyl 4-oxo-3-oxa-7, 11,16-triazaoctadecane-6,17,18-tricarboxylate, triethyl 4-oxo-3-oxa-7,14,21-triazatricosane-6,22,23-tricarboxylate, and Triethyl 4-oxo-3-oxa-7,11,15-triazaheptadecane-6,16, 17-tricarboxylate.

21. The method as claimed in claim 1, wherein the polyurea system comprises, as component C), organic fillers which have a viscosity at 23° C., measured in accordance with DIN 53019, in the range from 10 to 20 000 mPas and, as component D) water and/or a tertiary amine, where the tertiary amine is selected from the group consisting of triethanolamine, tetrakis(2-hydroxyethyl)ethylenediamine, N,N-dimethyl-2-(4-methylpiperazin-1-yl)ethanamine, 2-{[2-(dimethylamino)ethyl](methyl)amino}ethanol and 3,3',3"-(1,3,5-triazinane-1,3,5-triyl)tris(N,N-dimethylpropan-1-amine).

* * * * *